United States Patent [19]

Kano et al.

[11] Patent Number: 4,466,740
[45] Date of Patent: * Aug. 21, 1984

[54] PARTICLE AGGLUTINATION ANALYZING PLATE

[75] Inventors: Tokio Kano, Akishima; Akira Tamagawa, Hino, both of Japan

[73] Assignee: Olympus Optical Co., Ltd., Japan

[*] Notice: The portion of the term of this patent subsequent to Dec. 1, 1998 has been disclaimed.

[21] Appl. No.: 309,414

[22] Filed: Oct. 7, 1981

[30] Foreign Application Priority Data

Oct. 9, 1980 [JP] Japan .................................. 55-141175

[51] Int. Cl.³ .............................................. G01N 1/10
[52] U.S. Cl. ........................................ 356/246; 356/38; 356/39; 422/73; 422/102
[58] Field of Search ............... 356/38, 39, 335, 244, 356/246; 350/536; 422/73, 102

[56] References Cited

U.S. PATENT DOCUMENTS

| | | | |
|---|---|---|---|
| 3,432,275 | 3/1969 | Unger | 356/246 X |
| 3,656,833 | 4/1972 | Wallace | 356/246 X |
| 3,770,380 | 11/1973 | Smith | 356/39 X |
| 3,773,426 | 11/1973 | Mudd | 356/246 X |
| 4,245,052 | 1/1981 | Lund | 356/246 X |
| 4,290,997 | 9/1981 | Suovaniemi | 356/246 X |
| 4,303,616 | 12/1981 | Kano et al. | 356/246 X |

Primary Examiner—William L. Sikes
Assistant Examiner—Matthew W. Koren
Attorney, Agent, or Firm—Parkhurst & Oliff

[57] ABSTRACT

A plate for use in an immunological analysis on the basis of agglutination reaction of particles, has formed therein a number of reaction vessels each having a conical bottom surface. The plate is formed by molding of chemically resistive acrylic resins. Each vessel has an inclined bottom surface and a plurality of concentric protrusions or depressions are formed in the bottom surface to allow formation of a stable basic layer of settled particles, which basic layer can assure the formation of clear and precise particle patterns on the bottom surface.

15 Claims, 14 Drawing Figures

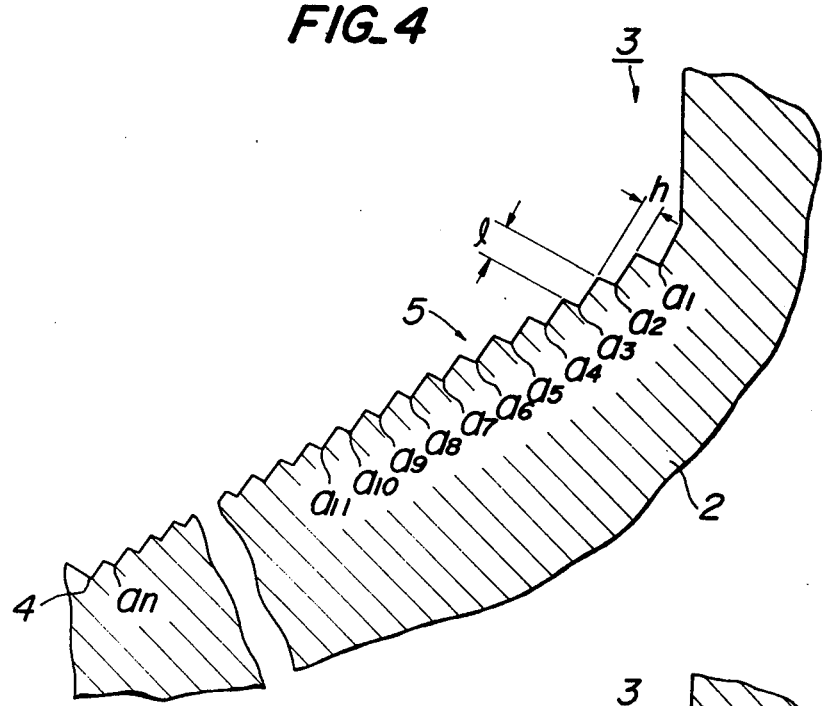
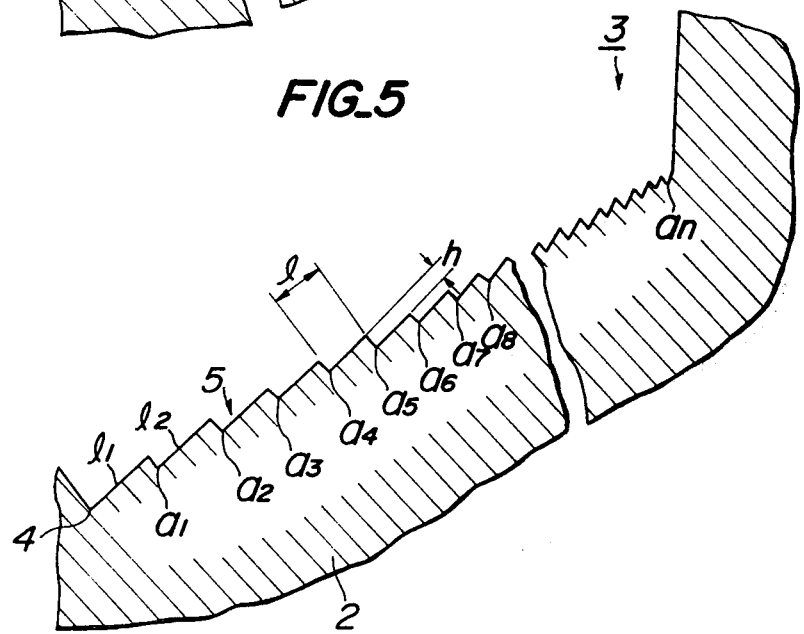

PARTICLE AGGLUTINATION ANALYZING PLATE

BACKGROUND OF THE INVENTION

This invention relates to an agglutination analyzing vessel for analyzing agglutination patterns produced in response to immunological agglutination reaction and more particularly to a plate comprising a number of vessels for identifying various kinds of blood types with the aid of agglutination patterns of blood corpuscles or for detecting various kinds of antibodies and various antigens in sample solutions (like viruses, proteins and the like) with the aid of agglutination patterns of not only blood corpuscles but also of particles of material such as latex, carbon and the like.

In the conventional method of identifying blood types, for example, use is made of a winecup-shaped reaction vessel into which are quantitatively introduced a sample solution, 2 to 5% of test blood corpuscles suspended in saline solution, and a specified antiserum. Then, the mixture is set stationary to allow reaction between blood corpuscles and antiserum. Subsequently, it is centrifuged to sediment blood corpuscles. Then, the reaction vessel is rapidly wobbled so that the sedimented blood corpuscles are forcedly separated from one another. Then it is relatively slowly wobbled so as to collect the agglutinated particles at the center portion of the bottom surface of the vessel and form agglutinated patterns, to allow photometric detection of these patterns.

Such conventional blood type identifying method in which sedimentation is effected and then the reaction vessel is rapidly wobbled so as to separate the sedimented blood corpuscles from the bottom surface of the vessel can only be applied to the analysis of regular ABO blood type which shows strong agglutination, but could not be applied to many other immunological agglutination reactions which show weak agglutination, for example, a method of determining Rh blood subtype or detecting various kinds of incomplete antibodies. That is, if the agglutination reaction is weak, the blood corpuscles which have been clumped together become separated from each other when the reaction vessel is wobbled, and as a result, the particles are not collected at the lowest center portion of the reaction vessel.

In order to avoid the above mentioned drawback, the applicant has proposed in Japanese Patent Application No. 54-53,370 a method of identifying a blood type, by means of which the blood type showing weak agglutination due to incomplete antibodies as well as the blood type showing strong agglutination due to natural antibodies can be identified accurately. In this method, use is made of a cylindrical reaction vessel having a conical bottom and given amounts of blood corpuscles and antiserum are delivered into the vessel. After these substances are mixed, they are left to stand for a relatively short time, such as a half hour, and then the particle pattern formed on the bottom is detected to identify the blood type. In this method, when the blood corpuscles to be tested and the antibody react upon each other, the agglutinated blood cells are deposited over the whole bottom surface, like snow, but when the blood corpuscles do not react upon the antibody, the blood corpuscles are not agglutinated and settle down on the bottom separately and roll down the inclined bottom surface. Therefore, almost all corpuscles are collected at the lowest center portion of the bottom. In this manner, the pattern formed on the bottom by the settled blood corpuscles becomes different, depending upon the existence of agglutinating reaction between the blood corpuscles and antibody. Thus, by detecting the pattern on the bottom, it is possible to identify the blood type. The inventors have conducted various tests with using such a vessel and sometimes have encountered a problem that even in the agglutinating reaction, the agglutinated corpuscles slide down along the inclined bottom surface into the bottom center. In this case, it is difficult to determine the blood type accurately.

There has been also known a micro-plate having a number of cylindrical reaction vessels each having a concave or conical bottom from, for instance, German Patent Application Laid-open Publication No. 2,915,145. However, in the known micro-plate the above problem also occurs and particularly the weakly agglutinated corpuscles slide down the bottom surface into its center. Therefore, the agglutination patterns could not be formed precisely.

SUMMARY OF THE INVENTION

The present invention has for its object to provide a novel and useful plate comprising a number of reaction vessels by means of which clear and precise agglutination patterns of settled particles can be formed on bottom surfaces of the vessels, even if agglutinating reactions are weak.

According to the invention, in a plate having a plurality of reaction vessels each including an inclined bottom surface wherein particles can settle down along said bottom surface so as to form agglutination patterns on the bottom surface of the vessel to thereby effect an immunological analysis, the improvement comprises a plurality of steps formed in the bottom surface of the respective reaction vessels, said steps having such shape and dimension to permit the formation of a stable basic layer of the particles settled on the bottom surface.

The present invention is based on a recognition of the fact that in order to form clear and precise agglutination patterns on the bottom surface of reaction vessel, it is very effective to form a stable and continuous basic layer of the settled particles. Once such a basic layer has been formed on the bottom surface, the descending agglutinated particles are stably deposited on the layer, but the descending separate particles slide or roll down along the basic layer and are gathered at the lowest bottom portion.

BRIEF DESCRIPTION OF THE DRAWINGS

FIGS. 4, 5 and 6 are enlarged cross sectional views illustrating three embodiments of the bottom surface construction according to the invention;

DETAILED DESCRIPTION OF THE PREFERRED EMBODIMENTS

Figure 1:
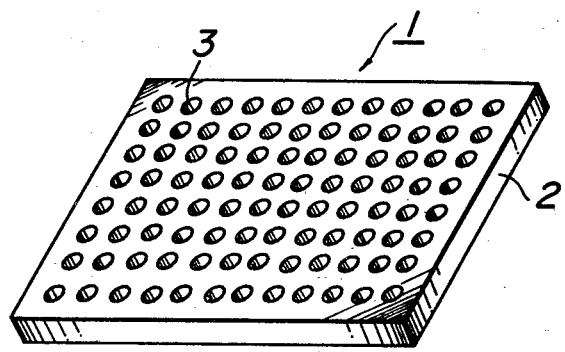
FIG. 1 is a perspective view showing the plate having a number of reaction vessels according to the invention.

In the agglutination analyzing plate according to the invention, the steps function to deposit and hold the stable basic layer of settled particles on the inclined bottom surface irrespective of the strength of the bonding force of the particles. In the following, the term steps shall be understood to include grooves, protrusions, depressions and combinations thereof. The inventors have ascertained that in order to form the clear and precise agglutination pattern on the bottom surface of the vessel in the case when agglutination reaction takes place, it is necessary to form a stable basic layer consisting of a continuous thin layer of deposited particles.

That is, if such a stable basic layer is formed, the particles agglutinated due to antigen-antibody reaction are deposited and held on the inclined bottom surface of the vessel in a stable manner, thereby forming clear and precise agglutination patterns. In accordance with the invention, the steps are formed in the bottom surface for the purpose of forming the above mentioned stable basic layer. This stable basic layer is formed even when the settling down particles are not agglutinated. When the settling down particles are not agglutinated, they slide down along the basic layer and are collected at the lowest portion of the bottom. As a result, it is always possible to form stable patterns irrespective of agglutination and non-agglutination of the settling down particles and precisely analyze various agglutinations.

The dimension of the steps formed in the inclined bottom surface of the respective reaction vessels is dependent on the size of the settling down particles. That is, if the steps are too large as compared with the size of the settling down particles, the particles not agglutinated are collected at the steps, and hence are prevented from sliding down toward the lowest point of the bottom. On the contrary, if the steps are too small as compared with the size of the settling down particles, and particularly if the agglutinating force of the particles is weak, the particles slide over the steps and are collected in the lowest point of the inclined bottom surface. As a result, it is impossible to form the stable basic layer and hence to discriminate the agglutination patterns precisely.

As described above, in the present invention, in order to eliminate such disadvantage, the inclined bottom surface of the respective vessels is provided with a plurality of the steps. It is preferable that the plurality of steps are composed of a plurality of elongated depressions each having a maximum depth of 2 to 50 $\mu$m and a width in the inclined direction of 5 to 200 $\mu$m for blood cells of human beings and sheep. Such depressions may be replaced by elongated protrusions each having a height of 2 to 50 $\mu$m and spaced apart from each other in the inclined direction by a distance of 5 to 200 $\mu$m.

If the maximum depth of the depression and the height of the protrusion are smaller than 2 $\mu$m, the settling down particles cannot be held by the depressions and protrusions. As a result, it is difficult to form the stable basic layer. Particularly, if the particles have a weak agglutinating force, the particles tend to be collected in the lowest point of the inclined bottom surface of the vessel irrespective of the agglutination or non-agglutination of the particles. As a result, it is difficult to discriminate the pattern produced when the particles are agglutinated from the pattern produced when the particles are not agglutinated.

If the maximum depth of the depression and the height of the protrusion exceed 50 $\mu$m, the settling down particles not agglutinated are held by such depressions and protrusions and thus, clear and precise patterns are not formed.

In addition, if the width of the depression and the distance between adjacent protrusions in the inclined direction are smaller than 5 $\mu$m, it is difficult to hold the settling down particles in a stable manner. Particularly, if the particles have a weak agglutinating force, the settling down particles tend to be collected in the lowest portion of the inclined bottom surface of the vessel irrespective of the agglutination or nonagglutination of the particles. As a result, it is difficult to discriminate the pattern produced when the particles are agglutinated from the pattern produced when the particles are not agglutinated.

If the width of the depression and the distance between adjacent protrusions in the inclined direction exceed 200 $\mu$m, the settling down particles tend to slip down along the inclined bottom surface of the vessel. As a result, it is impossible to form the stable basic layer and discriminate the pattern produced when the particles are agglutinated from the pattern produced when the particles are not agglutinated.

The invention will be now described with reference to the accompanying drawings.

FIG. 1 is a perspective view showing an embodiment of the plate according to the invention. The plate comprises a substrate 2 made of chemically resistive plastic material such as acrylic resins with an 8×12 matrix arrangement of reaction vessels 3. Such a plate 1 may be simply formed by molding. According to the invention, the respective vessels 3 each have an inclined bottom surface, and the bottom surface has formed therein a plurality of steps, such as grooves, protrusions and depressions.

Figure 2:
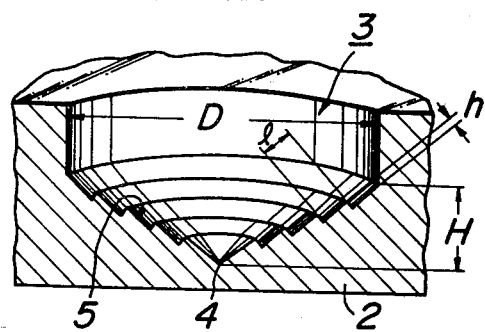
FIG. 2 is a cross sectional view showing one embodiment of a configuration of the vessel bottom according to the invention.
Figure 11:
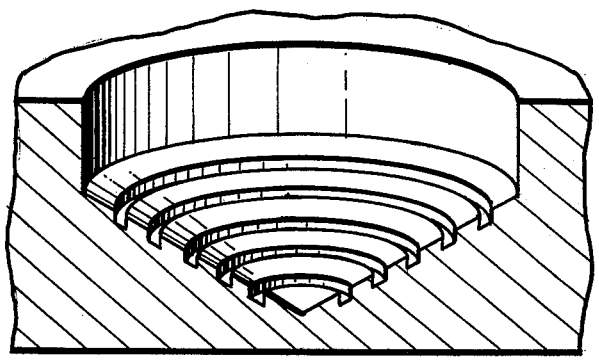
FIG. 11 is a cross-sectional view showing the vessel bottom of one embodiment according to the present invention.

FIG. 2 and 11 are enlarged cross section showing one embodiment of an agglutination analyzing vessel formed in the plate according to the invention. In the present embodiment, an agglutination analyzing vessel 3 is provided at its inclined bottom surface with a plurality of steps 5 formed by depressions, leading from the lowest point 4 of the inverted conical bottom surface of the vessel along the inclined bottom surface to the top periphery thereof located at substantially the middle point of the inner wall of the vessel. The steps are concentrically arranged about the lowest point 4 in a continuous and regular manner, the steps 5 being sawtooth-shaped in cross section taken along a radial direction of the vessel. The vessel 3 has an inner diameter D of 6 mm. The inverted conically inclined bottom surface has a height H of about 1.5 mm and is inclined by about 27° with respect to horizontal. Each depression has a maximum depth h of 2 to 50 $\mu$m and a width l in the inclined direction of 5 to 200 $\mu$m.

The vessel 3 constructed as above described makes it possible to maintain the sedimented particles such as blood corpuscles or the like on the depressed portions 5 and form a stable basic layer on the inclined bottom surface of the vessel 3. As a result, the agglutinated particles are effectively deposited on the stable basic layer. The sedimented particles not agglutinated slip down along the basic layer and are collected in the lowest point 4 of the inclined bottom, thereby always forming stable patterns. As a result, it is possible to discriminate difference between various agglutinations of the sedimented particles, thereby precisely effecting the immunological analysis.

Figure 3:
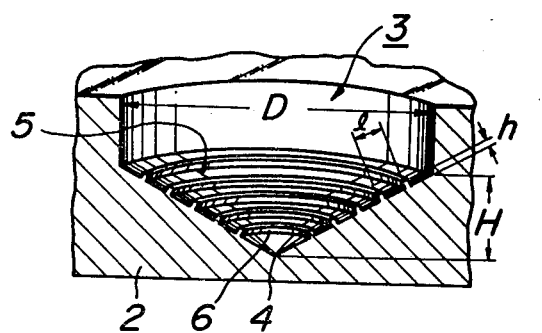
FIG. 3 is a cross sectional view showing another embodiment of the vessel bottom configuration according to the invention.

FIG. 3 shows another embodiment of an agglutination analyzing vessel formed in the plate according to the invention. In this embodiment, an agglutination analyzing vessel 3 is provided at its conically inclined bottom surface with a plurality of steps 5 formed by protrusions 6 leading from the lowest point 4 of the inverted conical surface along the inclined surface to the top periphery thereof, located at substantially the middle point of the inner wall of the vessel. These steps also are concentrically arranged about the bottom point 4 in a continuous and regular manner. Each protrusion 6 has a height h of 2 to 50 $\mu$m and a distance l between adjacent protrusions measured in the inclined direction of 5 to 200 $\mu$m. The inner diameter D of the vessel 3, height H and inclined angle of the inclined bottom surface with respect to horizontal are substantially the same as those shown in FIG. 2. The plate having such vessels 3 can be formed by molding of plastic material.

In the vessel 3 shown in FIG. 3, the protrusions 6 function to prevent the particles sedimented on the inclined bottom surface of the vessel from slipping down therealong toward the lowest point 4 of the bottom so as to form the stable basic layer on the inclined surface, thereby obtaining clear and precise agglutination patterns in the same manner as the previous embodiment.

In the embodiments shown in FIGS. 2 and 3, the steps 5 formed by the depressed portions and protruded portions 6 are arranged along a substantially overall inclined base surface region of the vessel. But, these depressed and protruded portions may be arranged along only a portion of the inclined bottom surface of the vessel. Further the protrusions 6 in the vessel of FIG. 3 may be replaced by grooves or elongated depressions.

FIG. 4 is an enlarged cross section showing another embodiment of the configuration of the bottom surface of the vessel formed in the plate according to the invention. In this embodiment, the steps 5 are formed by depressions $a_1$ to $a_n$ in a similar manner as the embodiment shown in FIG. 2, but the widths l and depths h of these depressions are not equal to each other, but are made different in the direction of the inclined surface. That is to say, the depths h of the depressions $a_1, a_2, \ldots, a_n$ are made successively smaller toward the bottom center 4 and the widths l of the depressions are also made successively smaller toward the bottom center 4, within the above mentioned range of 5 to 200 $\mu$m. For instance, in the plate used for analyzing human blood cells, the outermost depression $a_1$ has a depth h of 20 $\mu$m, and the depths h of the depressions $a_2$ to $a_{10}$ are made successively smaller by 1 $\mu$m. Then the depth of the tenth depression $a_{10}$ becomes 11 $\mu$m. The depths of the remaining depressions $a_{11}$ to $a_n$ are made equal to each other and set at 10 $\mu$m. In case of the plate for sheep blood cells, the depth h of the outermost depression $a_1$ is set at 12 $\mu$m, and the depths of the depressions up to the seventh depression $a_7$ are made progressively smaller by 1 $\mu$m. Then the depth of the seventh depression $a_7$ becomes 6 $\mu$m. The depths of the remaining depressions $a_8$ to $a_n$ are set at a constant value of 5 $\mu$m. In another embodiment of the plate for the human blood cells, the depth h of the outermost depression $a_1$ is selected at 20 $\mu$m and the depths of the depressions $a_2$ to $a_8$ are successively decreased by 1 $\mu$m and the depths of the remaining depressions $a_9$ to $a_n$ are set at a constant value of 12 $\mu$m.

FIG. 5 is an enlarged cross sectional view showing another embodiment of the configuration of the bottom surface of the vessel formed in the plate according to the invention. Also in this embodiment the steps 5 are formed by a number of depressions $a_1$ to $a_n$, but in this embodiment the depths h and the widths l of the depressions are made successively smaller from the bottom center 4 to the periphery of the vessel 3 within the above ranges of 2 to 50 $\mu$m and 5 to 200 $\mu$m, respectively. For instance, the width $l_1$ of the innermost depression $a_1$ among twenty depressions $a_1$ to $a_{20}$ is set at 150 $\mu$m and the widths $l_2, l_3, \ldots, l_{20}$ of the successive depressions $a_2$ to $a_{20}$ are successively decreased by 5 $\mu$m and thus, the width $l_{20}$ of the outermost depression $a_{20}$ becomes 50 $\mu$m.

Figure 6:
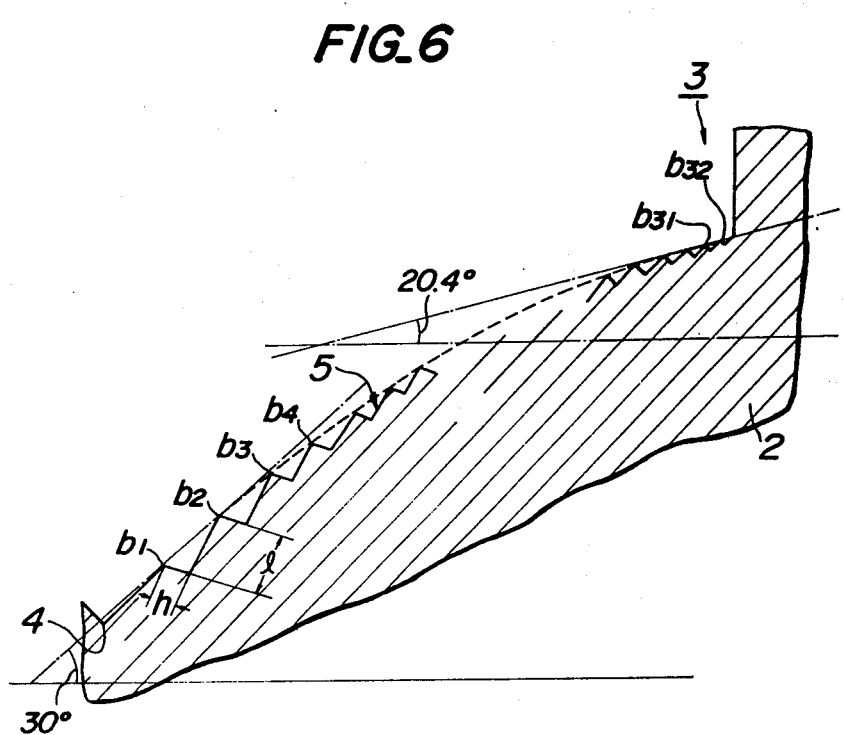

In the embodiment shown in FIG. 6, thirty two steps 5 are formed by thirty two concentric depressions formed in the inclined bottom surface of the vessel 3 of the plate according to the invention. In this embodiment, the depths h and widths l of the depressions are made progressively smaller from the bottom center 4 to the periphery within the above ranges of 2 to 50 $\mu$m and 5 to 200 $\mu$m, respectively. For instance, a line connecting a top $b_1$ of the innermost step and a top $b_2$ of the next step makes an angle of 30° with respect to horizontal, a line connecting next successive tops $b_2$ and $b_3$ is inclined by 29.7° from horizontal, a line connecting next successive tops $b_3$ and $b_4$ makes an angle of 29.4° with respect to horizontal, and so on. In this manner angles between horizontal and lines connecting two successive tops up to the outermost top $b_{32}$ are progressively made smaller by an angle of 0.3° and thus become 29.1°, 28.8°, 28.5°, 28.2°, ..., 21.9°, 21.6°, 21.3°, 21.0°, 20.7° and 20.4°. Therefore, the inclination angle of the bottom surface becomes smaller toward the periphery. It should be noted that if the slope of the bottom surface is made too steep, the agglutinated particle pattern might be slide downwardly, while if the inclination angle is made too small, the particles are hardly agglutinated and further the non-agglutinated particles hardly roll down the bottom surface. Thus, it takes a rather long time for the particles to arrive at the bottom center. The experimental tests show that the steep slope near the bottom center is preferably set between 25° and 45° and the gentle slope near the periphery is preferably selected between 15° and 30°. In general, when the inclined angle is made smaller, the particles do not smoothly slide down the slope and thus, the accuracy of the detection will be increased although the test time is liable to be longer. Contrary to this, when the inclination angle is made large, non-agglutinated particles roll down the slope quickly and thus, the analyzing time can be shortened. According to the invention the inclination angle of the bottom surface may be determined to values within the above mentioned ranges in accordance with respective analyses.

Figure 7:
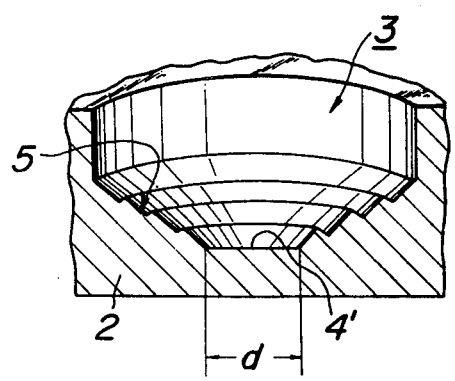
FIG. 7 is a cross sectional view showing still another embodiment of the bottom configuration according to the invention.

In an embodiment shown in FIG. 7, the lowermost bottom portion 4' of the vessel 3 formed in the substrate 2 of the plate 1 is not made conical, but is made flat over a distance d. It has been experimentally confirmed that the diameter d of the flat bottom portion 4' is preferably set to 0.1–1.0 mm. It should be noted that even when the blood cells react upon the antiserum, some cells are not agglutinated and roll down the bottom surface into the bottom center. Therefore, the judgement of the agglutination and non-agglutination might be inaccurate. The plate shown in FIG. 7 can effectively overcome such a disadvantage, because the flat bottom center 4' can at least partially avoid the formation of a thick blood cell layer in the agglutination reaction.

Figure 8:
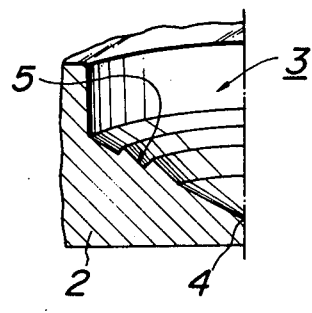
FIGS. 8, 9 and 10 are cross sectional views illustrating still other embodiments of the bottom surface configuration according to the invention.
Figure 9:
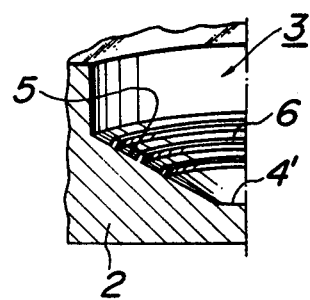
Figure 10:
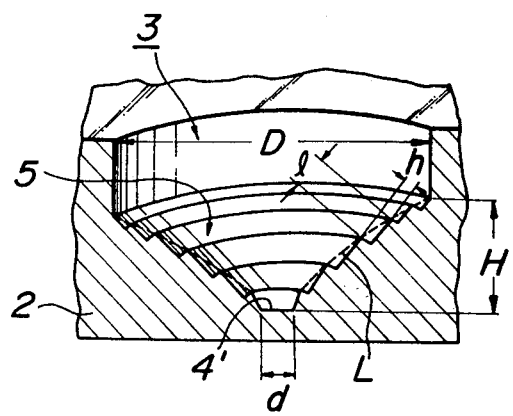

The present invention is not limited to the embodiments explained above, but may be modified in various forms. For instance, in an embodiment illustrated in FIG. 8, the steps 5 are formed not in the entire bottom surface of the vessel 3, but in a part thereof. Also in an embodiment shown in FIG. 9, the concentric protrusions 6 are formed only in a part of the inclined bottom surface of the vessel 3 formed in the substrate 2. Further in this embodiment, the center portion 4' of the bottom is flattened like the embodiment illustrated in FIG. 7. In this manner, according to the invention, it is possible to form the inclined bottom surface of the vessel into combined forms of the above embodiments. For instance, in an embodiment shown in FIG. 10, the bottom surface of the vessel 3 is formed as a combination of the embodiments illustrated in FIGS. 5, 6 and 7. Of course, other combinations may be conceived.

Figure 12:
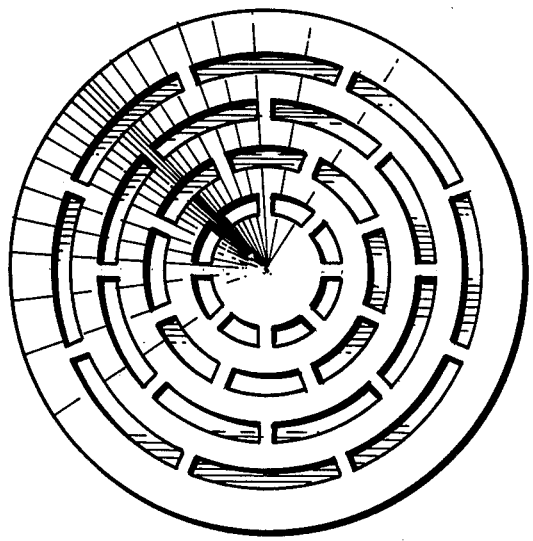
FIG. 12 is a top view of one embodiment according to the present invention.
Figure 14:
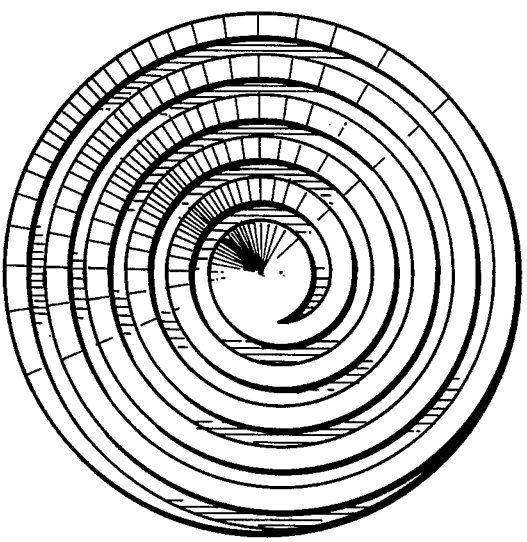
FIG. 14 is a top view of one embodiment according to the present invention.
Figure 13:
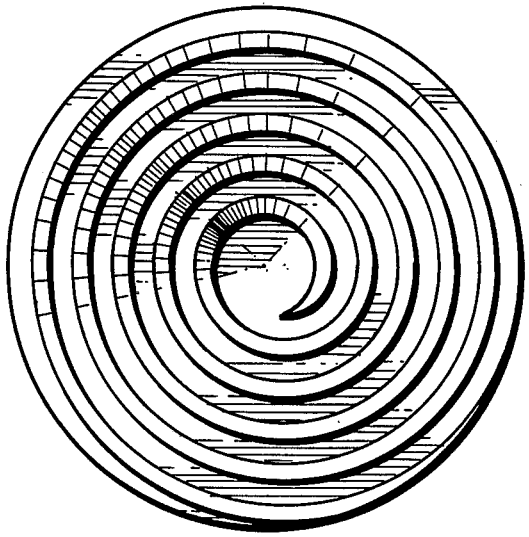
FIG. 13 is a top view of one embodiment according to the present invention.

Further, the number of the vessels formed in the plate is not limited to 8×12, but any other number of vessels may be formed. The inner diameter D of the vessel and the height H of the inclined bottom surface may be set to any desired values. Moreover, the general configuration of the bottom surface of vessel is not limited to the conical and frustoconical shapes, but may be formed in any other shapes such as semiconical, semi-frusto-conical, polyhedral and frusto-polyhedral. The steps may be constituted by combinations of depressions and protrusions. Further, in the above embodiments, the steps are formed as concentrical ring-shaped depressions and protrusions, but may be formed by intermittent depressions and protrusions as shown in FIG. 12. These intermittent depressions and protrusions may be arranged in a zigzag in the inclined direction. Further, a spiral protrusion or depression as shown in FIGS. 13 and 14 respectively may be formed in the bottom surface. Moreover, it is not always necessary to form in the plate a number of vessels having the same shape and dimensions, but vessels of different shapes and/or sizes may be formed in the single plate. By means of such a plate, it is possible to treat particles having different sizes simultaneously.

According to the invention the plate comprises a number of reaction vessels each having an inclined bottom surface in which a plurality of protrusions and/or depressions are formed and the stable basic layer of settled particles is formed on the inclined bottom surface. Therefore, analyses of a number of samples can be carried out effectively by means of the single plate and the determination of the various blood types due to the strong and weak agglutinations can be effected accurately by means of the clear and precise agglutination and non-agglutination patterns. Such clear patterns can be easily and accurately detected by naked eyes as well as photoelectric devices. Moreover, the plate having a number of reaction vessels can be manufactured simply and economically by molding. In an automatic analyzer, the plate with a number of vessels may be simply and positively fed and also washed. Further, the particle patterns formed on the bottom surfaces of a plurality of vessels may be simultaneously detected by a photoelectric device. In case of photoelectrically detecting the particle patterns, the photoelectric device may be either of the transmission or reflection type. In the transmission type, the plate is made of transparent material, and in the reflection type, the bottom surfaces of vessels may be made white or may be coated with highly reflective optical material.

What is claimed is:

1. A particle agglutination analyzing plate, comprising:
   a plurality of reaction vessels, each having an inclined bottom surface, formed in said plate;
   a plurality of steps formed in the bottom surface of each of said reaction vessels, said steps having a dimension measured perpendicularly to the inclined bottom surface of 2 to 5 μm and a pitch measured in the inclined bottom surface of 5 to 200 μm.

2. The particle agglutination analyzing plate according to claim 1, wherein said plurality of steps are formed by a plurality of depressions each having a depth of 2 to 50 μm and a width in the inclined direction of 5 to 200 μm.

3. The particle agglutination analyzing plate according to claim 2, wherein said plurality of depressions are of sawtooth shape.

4. The particle agglutination analyzing plate according to claim 1, wherein said plurality of steps are formed by a plurality of protrusions each having a height of 2 to 50 μm and spaced apart from each other in the inclined direction by a distance of 5 to 200 μm.

5. The particle agglutination analyzing plate according to claim 1, wherein said bottom surface has a periphery and a lowest portion, wherein the depths and widths of the steps are gradually decreased from the periphery to the lowest portion of the bottom surface.

6. The particle agglutination analyzing plate according to claim 1, wherein said bottom surface has a periphery and a lowest portion, wherein the depths and widths of the steps are gradually increased from the periphery to the lowest portion of the bottom surface.

7. The particle agglutination analyzing plate according to claim 1, wherein said bottom surface has a periphery and a lowest portion, wherein angles between a horizontal plane and lines connecting successive tops of successively adjacent steps are gradually decreased from the lowest portion to the periphery of the inclined bottom surface.

8. The particle agglutination analyzing plate according to claim 7, wherein said angles near the lowest portion and the periphery are set at 25°–45° and 15°–30°, respectively.

9. The particle agglutination analyzing plate according to claim 1, wherein said plate is formed of a molded, chemically resistive material.

10. The particle agglutination analyzing plate according to claim 1, wherein the plate comprises a plurality of vessels having different shapes and/or dimensions.

11. A plate according to claim 1, wherein said bottom surface has the shape of an inverted cone, and said plurality of steps are formed substantially from the lowest point of the inverted cone to the outer periphery of the inverted cone, and are arranged regularly and concentrically about the lowest point.

12. The particle agglutination analyzing plate according to claim, 11 wherein said lowest point of the inverted bottom surface of the vessel is flattened.

13. A plate according to claim 1, wherein said bottom surface has the shape of an inverted cone, and said plurality of steps are arranged concentrically and intermittently about the lowest point of the inverted cone.

14. A plate according to claim 1, wherein said plurality of steps are formed by a single spiral depression.

15. A plate according to claim 1, wherein said plurality of steps are formed by a single spiral protrusion.

* * * * *